United States Patent [19]

Rosenbluth

[11] Patent Number: 4,762,128
[45] Date of Patent: Aug. 9, 1988

[54] METHOD AND APPARATUS FOR TREATING HYPERTROPHY OF THE PROSTATE GLAND

[75] Inventor: Robert F. Rosenbluth, Laguna Niguel, Calif.

[73] Assignee: Advanced Surgical Intervention, Inc., San Clemente, Calif.

[21] Appl. No.: 939,754

[22] Filed: Dec. 9, 1986

[51] Int. Cl.[4] ..................... A61M 25/00; A61M 29/02
[52] U.S. Cl. .................................. 128/343; 128/344; 604/96
[58] Field of Search ................................. 604/96–103; 128/325, 341–345, 348.1

[56] References Cited

U.S. PATENT DOCUMENTS

| | | | |
|---|---|---|---|
| 4,560,374 | 12/1985 | Hammerslag | 128/344 X |
| 4,580,568 | 4/1986 | Gianturco | 604/96 X |
| 4,641,653 | 2/1987 | Rockey | 128/344 |
| 4,649,922 | 3/1987 | Wiktor | 128/344 |
| 4,655,771 | 4/1987 | Wallsten | 128/343 X |
| 4,660,560 | 4/1987 | Klein | 128/344 |

FOREIGN PATENT DOCUMENTS 1205743 9/1970 United Kingdom ................ 128/343

Primary Examiner—Dalton L. Truluck
Attorney, Agent, or Firm—Knobbe, Martens, Olson & Bear

[57] ABSTRACT

Disclosed is a method and apparatus for treatment of hypertrophy of the prostate gland. The apparatus comprises an expansion catheter having an expandable tubular stent associated therewith, adapted for transurethral insertion via the external opening of the urethra and placement within a stenotic region of the urethral lumen caused by a hypertrophied prostate gland. Force exterted by the expansion catheter upon the tubular expandable stent causes an opening of the lumen within the prostatic urethra. Removal of the expansion catheter, leaving in place the expanded tubular stent, ensures long-term patency of the urethral lumen. Also disclosed is an apparatus for reducing in diameter and thereafter removing a previously implanted and expanded tubular stent made and inserted in accordance with the present invention.

28 Claims, 4 Drawing Sheets

U.S. Patent  Aug. 9, 1988  Sheet 1 of 4  4,762,128
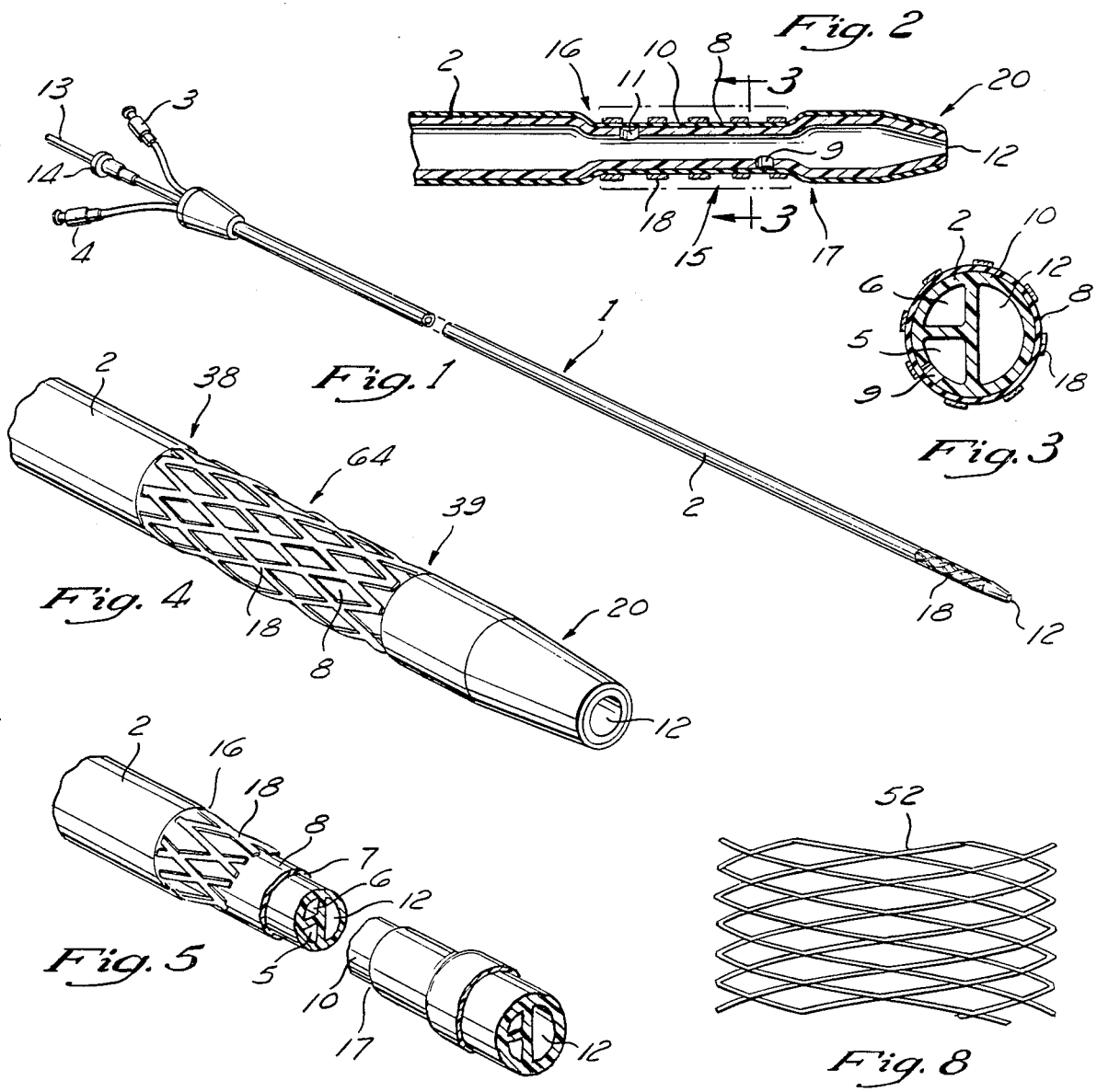

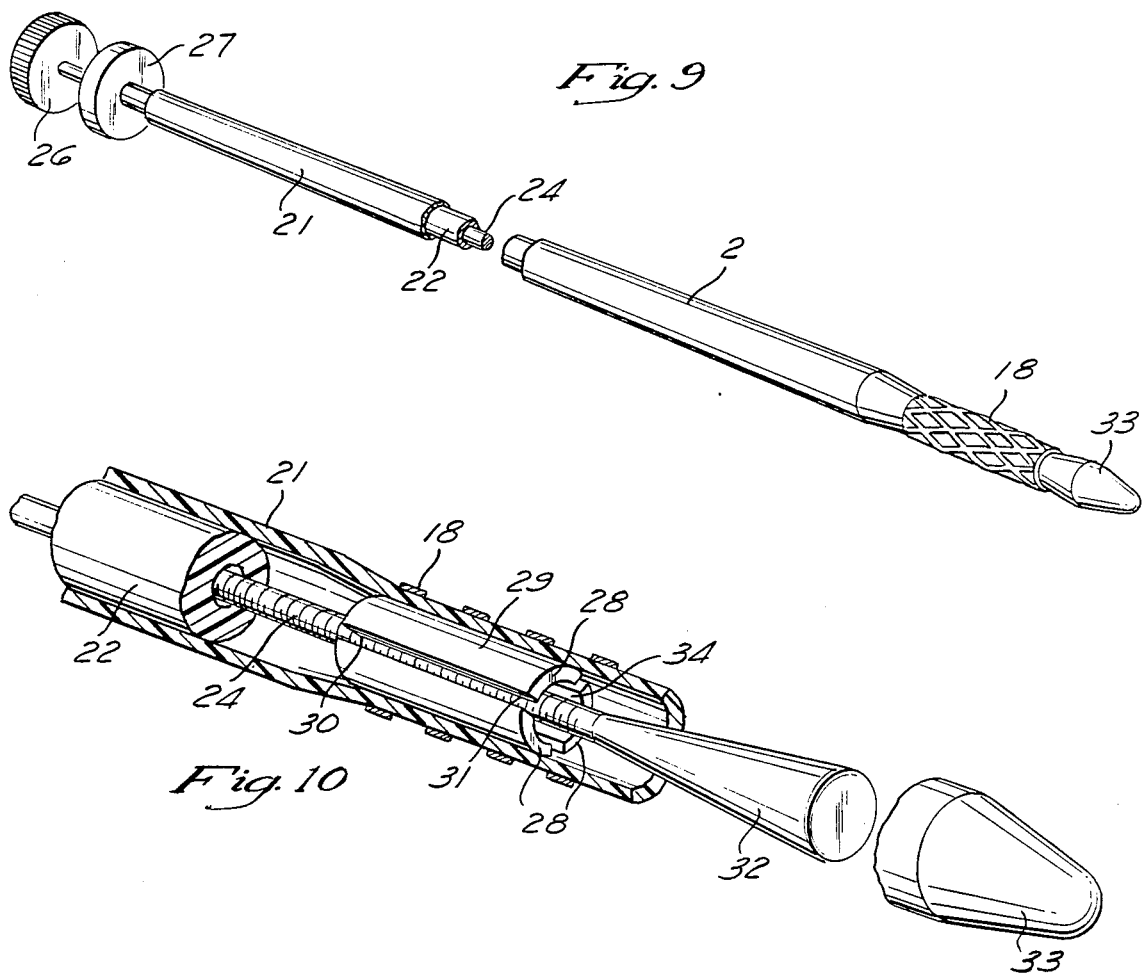

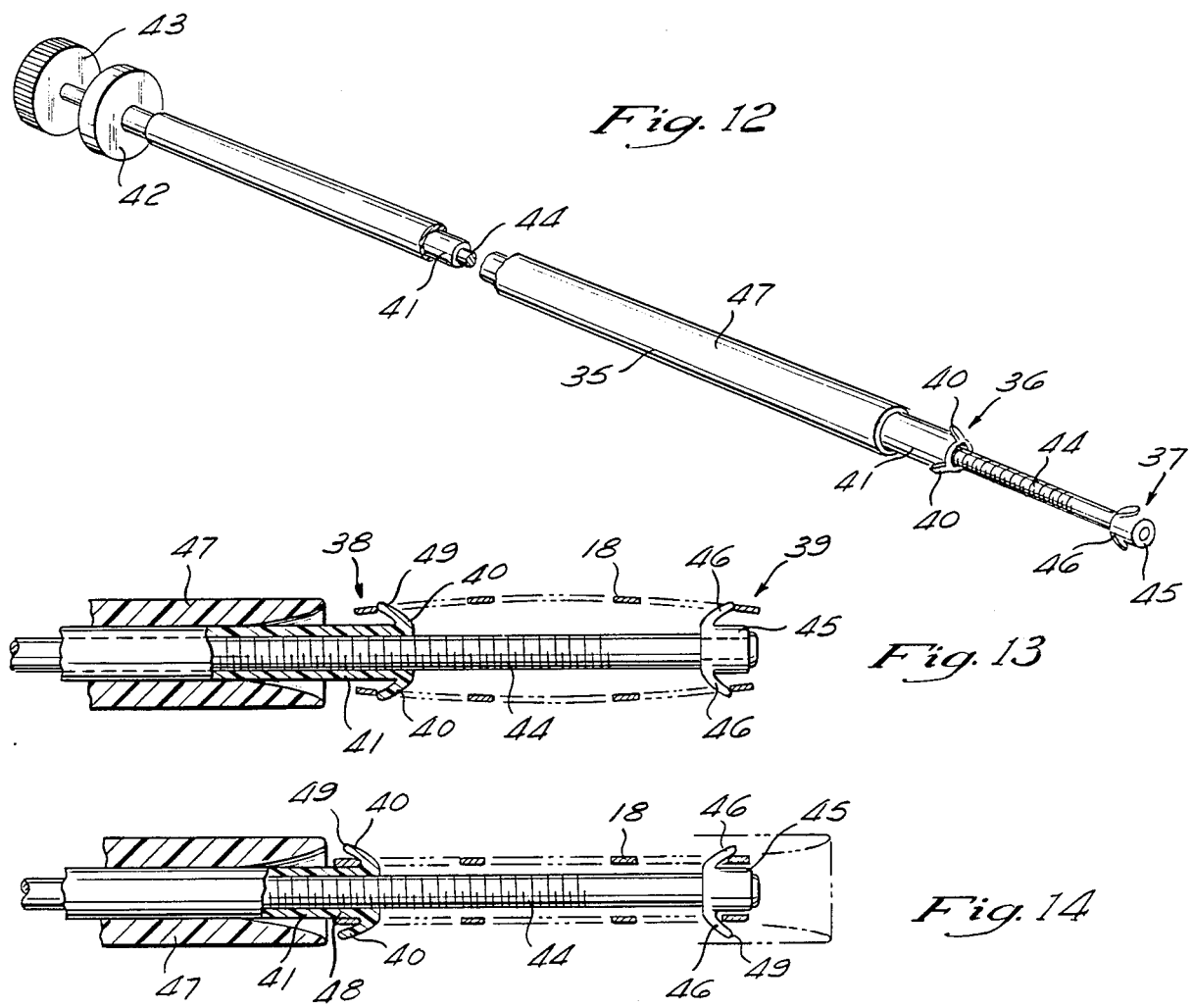

METHOD AND APPARATUS FOR TREATING HYPERTROPHY OF THE PROSTATE GLAND

BACKGROUND OF THE INVENTION

The surgical treatment of hypertrophy of the prostate gland has been a routine procedure in the operating room for many years. One method of surgical treatment is open prostectomy whereby an incision is made to expose the enlarged prostate gland and the hypertrophied tissue is removed under direct vision. Another method, which has gained increasing usage in recent years, is transurethral resection. In this procedure, an instrument called a resectoscope is placed into the external opening of the urethra and an electrosurgical loop is used to carve away sections of the prostate gland from within the prostatic urethra under endoscopic vision. For an interesting historical survey of prostate surgery see the book "Benign Prostatic Hypertrophy" edited by Frank Hinman, M.D. and particularly the chapter entitled "Prostectomy, Past and Present" by Geoffrey D. Chisholm, M.D.

The technique of transurethral resection offers many benefits to the patient as compared to open prostectomy. Using this technique the trained urologist can remove the hypertrophied prostate with less discomfort, a shorter hospital stay, and lower rates of mortality and morbidity. Over 333,000 patients underwent this procedure in the United States in 1985, with an average length of stay in the hospital of six days.

Notwithstanding the significant improvement in patient care resulting from the widespread application of transurethral resection, there remains a need for a less invasive method of treating the symptoms of prostate disease. Various complications including impotence, incontinence, bleeding, infection, residual urethral obstruction, urethral stricture, and retrograde ejaculation may affect the patient following transurethral resection. A less invasive procedure which would reduce or eliminate the occurence of these complications and reduce the hospital stay and resulting costs would be of significant value.

One of the earliest applied methods of relieving the acute urinary retention symptomatic of prostate disease was the placement of a catheter through the external urethra opening into the bladder thereby allowing the outflow of urine from the bladder by way of the catheter lumen. These urinary catheters typically employ a balloon at the tip which, when inflated, prevent the expulsion of the catheter from the body. Although this method is effective in achieving urinary outflow, it is generally unacceptable as a long term treatment due to problems of infection, interference with sexual activity, and maintenance and change of catheters.

The use of dilating bougies and sounds for mechanical dilation of the prostatic urethra has been attempted without success in the treatment of prostatic hypertrophy. The fibrous tissue of the prostate gland rebounds after dilation, resulting in only a temporary reduction of urethral constriction. A method of treating prostate disease involving the application of balloon dilatation in a similar manner as in percutaneous transluminal angioplasty of arterial occlusions has been proposed in an article in the September 1984 issue of Radiology, page 655 entitled "Prostatic Hyperplasia: Radiological Intervention" by H. Joachim Burhenne, M.D., et al. This method of prostate dilation can be expected to have only a short term alleviation of urinary retention as the fibrous and resilient hypertrophied prostate gland will in a relatively short period of time cause the constriction of the prostatic urethra to recur. Also in the angioplasty arts, Palmaz, et al. have described the percutaneous, sheathed insertion of an expandable endoprosthesis into various major arteries of dogs in the article "Expandable Intraluminal Graft: A Preliminary Study" in the July 1985 issue of *Radiology* at page 73.

In contrast to the failure of dilation means to achieve lasting relief of the symptoms of prostatic hyperplasia, the use of bougie, sound, and balloon dilation has achieved moderate success in the treatment of ureteral strictures and non-prostatic urethral strictures. See, for example, the abstract entitled "Self Intermittent Dilation Program via Coaxial Balloon Urethral Dilator" by J. D. Giesy et al. published in the April, 1985 issue of the Journal of Urology. The contrasting lack of success achieved by dilation in the prostatic urethra is believed to be a function of the differing etiology of the disease. Strictures in the urethra outside of the prostate region are generally due to pathology of the wall and lining of the urethra. Dilation of the urethral wall, in these strictures, causes an enlargement of the urethral lumen through deformation of the urethral wall and lining. In contrast, urethral stenosis resulting from prostatic hypertrophy, is a disease of the enlarged, fibrous, and resilient tissue of the prostate gland. Deformation of the urethral wall will have no lasting effect on relieving the stenosis as the cause of the stenosis is pressure exerted by the hypertrophied prostate gland which, due to its resilient fibrous structure and large bulk, will tend to rebound after temporary compression.

It is important that a method for prostate dilatation, in order to be effective, incorporate means of maintaining the patency of the urethral lumen. Without such means, the patient would be subject to periodically repeated procedures in order to maintain urinary flow.

SUMMARY OF THE INVENTION

The present invention provides a method of relieving the urinary retention symptomatic of hypertrophy of the prostate gland, which requires little or no hospitalization, and which is unattended by the adverse side effects associated with transurethral resection and other surgical techniques. In addition, the present invention provides a method for dilatation of the prostatic urethra which will insure long term patency of the urethral lumen.

Thus, there has been provided in accordance with one aspect of the present invention a method for treating hypertrophy of the prostate gland, which comprises the steps of transurethrally inserting and positioning a dilatation means having an expandable tubular stent associated therewith within a restricted portion of the urethra and dilating the stent with said dilatation means to a predetermined maximum external diameter and configuration. The exterior configuration of the apparatus of the present invention enables insertion thereof without the use of a sheath, and with the tubular stent substantially totally exposed to the wall of the urethra. Preferably, dilation of the stent and consequent dilation of the surrounding restricted portion of the urethral lumen is effected at least to the extent that it eliminates the stenosis. Thereafter, the dilatation means is returned to its undilated state and withdrawn through the lumen of the dilated tubular stent, leaving the dilated tubular stent within the previously restricted portion of the urethra, thereby restoring patency to the prostatic urethral lumen. Visualization of the placement step may be accomplished through the use of a radiopaque dye, in accordance with known techniques. Radiopaque markers on the catheter and radiopacity of the graft are also used to make the devices radiographically visible.

An additional aspect of the method of the present invention comprises the steps of reinserting a dilatation apparatus into the external opening of the urethra, positioning the dilation apparatus coaxially within a previously positioned and dilated tubular stent, expanding the dilatation apparatus, and thereafter reducing the diameter of and removing the dilatation apparatus leaving the expanded tubular stent within the urethra. Accordingly, an expandable tubular stent inserted in accordance with the method of the present invention may, at a later time, be further dilated or redilated.

Still a further aspect of the method of the present invention provides for the removal of a previously positioned stent. Removal is accomplished by transurethral insertion of a removal instrument comprising a first and second attachment means wherein the attachment means are axially spaced apart and are adapted to releasably engage the corresponding first and second axial ends of the stent. Once engaged, a force is applied to cause an axial elongation of the stent, and consequent reduction in diameter. Thereafter, the instrument and the radially reduced stent attached thereto may be removed.

In accordance with another aspect of the present invention there has been provided an apparatus for the treatment of prostatic hypertrophy comprising an expansion catheter having an expandable tubular stent associated therewith. The catheter comprises a radially expandable region near the distal end thereof which, in its unexpanded state, has an outer diameter that is smaller than the outer diameter of the adjacent region of the catheter. Thus, the collapsed expandable region forms the bottom of an annular depression about the catheter.

The stent is removably, coaxially disposed about the expandable region of the catheter and within the annular depression formed therearound, and is controllably radially outwardly expandable in response to pressure from the expandable region of the catheter. When the stent is coaxially disposed about the expandable region of the catheter, and in an unexpanded state, the outer diameter of the unexpanded stent is approximately the same as or less than the outer diameter of the adjacent region of the catheter. Preferably, the distal end of the catheter comprises a flexible, resilient material in a shape to facilitate insertion into and negotiation of a collapsed lumen with minimal trauma to the lining thereof.

A further aspect of the present invention provides a radially outwardly expandable tubular stent for restoring patency to a collapsed portion of the urethral lumen. Preferably, the stent comprises a material that is compatible with the urethral environment, and is capable of remaining in its expanded state following removal of the expansion catheter described above, thereby holding open the lumen of the urethra against a restricting pressure, such as that exerted by a hypertrophied prostate gland. The cross section of the expanded stent may be circular, or may also be a non-circular configuration which more closely corresponds to the shape of the normal lumen within the urethra. One embodiment of the stent in its expanded state comprises a substantially uniform cross-sectional area throughout it axial length. In another embodiment, the stent comprises a smaller cross-sectional area at its axial ends than in the central region thereof. In addition, the axial end regions of the stent may comprise a flexible material, or may taper in a radial inward direction thereby easing the transition from the lumen of the stent to the lumen of the urethra.

Further objects, features and advantages of the present invention will become apparent from the detailed description of preferred embodiments which follows, when considered together with the attached Figures.

BRIEF DESCRIPTION OF THE DRAWINGS

FIG. 1 is a perspective view of an apparatus according to the present invention, with the tubular stent in an unexpanded state.

FIG. 2 is a schematic detail view of the distal end of an apparatus according to the present invention, with the tubular stent in an unexpanded state.

FIG. 3 is a cross-sectional view taken along the line 3—3 in FIG. 2.

FIG. 4 is an enlarged, perspective view of the distal end of an apparatus in accordance with the present invention.

FIG. 5 is a perspective, sectional view of the distal end of an apparatus in accordance with the present invention.

FIG. 6 illustrates one embodiment of the side wall pattern of a tubular stent according to the present invention.

FIG. 7 is a cross-sectional view of a tubular stent of the present invention expanded to a configuration having a non-circular cross section.

FIG. 8 illustrates a modification of the side wall pattern illustrated in FIG. 6.

FIG. 9 is a perspective view of another embodiment of an expansion catheter according to the present invention.

FIG. 10 is a detailed perspective view of the distal end of the apparatus in FIG. 9.

FIG. 11 is an elevational, sectional view of the apparatus in FIG. 10.

FIG. 12 is a perspective view of a removal apparatus according to the present invention.

FIG. 13 is a sectional view of the removal apparatus of FIG. 12, engaging an expanded tubular stent.

FIG. 14 is a sectional view of the removal apparatus of FIG. 13, following axial elongation of the tubular stent.

FIG. 15 is a simplified schematic view of the apparatus of the present invention shown in FIG. 1, with a generally convex balloon and corresponding tubular stent illustrated in the expanded state.

DETAILED DESCRIPTION OF PREFERRED EMBODIMENTS

Expansion Catheter of FIGS. 1-5

Figure 16:
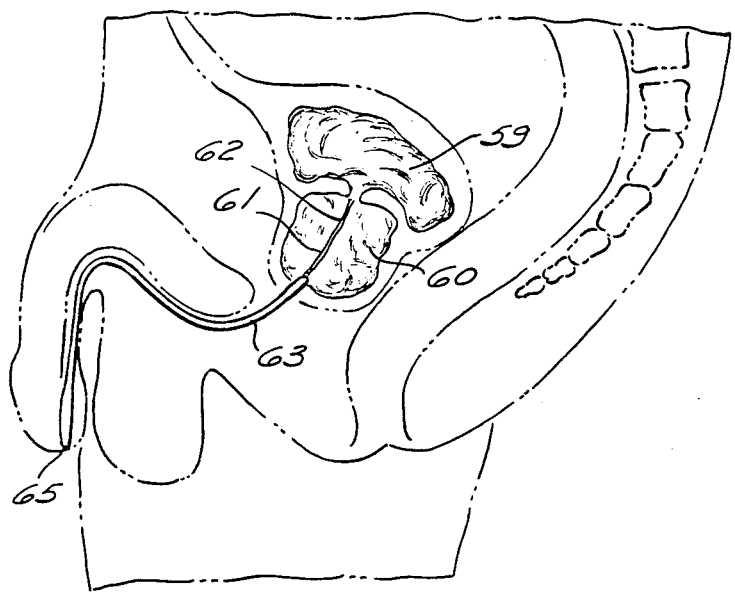
FIG. 16 is a simplified sectional view of the region of the male pelvis showing the urethra, prostate gland and bladder.

Referring to FIGS. 1-5 there is illustrated an expansion catheter 1 according to the present invention, which in this embodiment comprises a balloon catheter, having an axially elongate, catheter shaft 2. The proximal, control end of the catheter 1 may be equipped as would be the control end of known angioplasty balloon catheters such as that disclosed in U.S. Pat. No. 4,573,470 to Samson, et al. The embodiment of the present invention illustrated in FIG. 1 has an inflation port 3 and optimally a distinct vent port 4, each in fluid communication, respectively, with an inflation lumen 5 and a vent lumen 6 (illustrated in FIG. 3) extending axially through the catheter. Inflation lumen 5 is in fluid communication at the distal end thereof with the interior 7 of an expandable balloon 8 by means of at least one inflation duct 9 through the wall 10 of the catheter proximal lumen 5 and adjacent the interior surface of balloon 8. Similarly, vent lumen 6 is in fluid communication with the interior 7 of balloon 8 by means of at least one vent duct 11, proximal to inflation duct 9. At the commencement of filling the balloon, any air in the lumen 5, 6 or in the interior 7 of balloon 8 will be chased out of vent port 4, which may then be sealed by a stopcock or other means (not illustrated).

A third lumen 12 may be provided for receiving a radiopaque dye introduced by way of dye port 14 at the proximal end thereof. A guidewire 13 may also be inserted through dye port 14 and lumen 12.

Near the distal, functional end of the catheter, a region 10 of the catheter shaft 2 is reduced in diameter to provide an annular depression 15 defined axially by a proximal annular shoulder 16 and a distal annular shoulder 17 on catheter shaft 2. The axial length of the annular depression preferably corresponds to the desired length of a stent 18 to be inserted in a given application. Referring to FIG. 3, there is disposed concentrically about the reduced catheter wall 10 and at the radially inward most region of the annular depression 15, annular inflatable balloon 8 in fluid communication with said inflation lumen 5 by way of duct 9. An expandable, tubular stent 18 having a central lumen 19 therethrough (illustrated in FIG. 7), discussed infra, is coaxially disposed about the balloon 8.

The expansion catheter 1 of the present invention is designed so that the outer, substantially cylindrical profile of the catheter is uninterrupted by the presence of the expandable stent 18, in its unexpanded state. Accordingly, in the case of a balloon catheter, the outer diameter of the collapsed balloon 8 is smaller than the outer diameter of shoulders 16, 17 of the adjacent catheter shaft 2, so that the collapsed balloon 8 only partially fills the annular depression 15 formed between the annular shoulders 16, 17, in the radial direction. The unexpanded stent 18 is disposed coaxially about balloon 8 and between shoulders 16 and 17 such that the stent 18 and adjacent catheter shaft 2 comprise a substantially cylindrical configuration. This configuration enables insertion of the apparatus without the need for a sheath.

The material of the balloon 8 is in the form of a tubular sleeve which extends the length of the catheter 1 and is adhered to the wall of the catheter shaft 2 proximal to shoulder 16 and distal to shoulder 17 but not in the region 15 where it forms balloon 8 and is permitted to expand.

Introduction of pressurized fluid into the interior 7 of balloon 8 by way of inflation lumen 5 causes radial expansion of the balloon 8, which in turn causes a radial expansion of the stent 18 disposed concentrically therearound. Once expanded by inflating the balloon 8, the inner diameter of the central lumen 19 through expanded stent 18 is greater than the outer diameter of the catheter shaft 2 in the region between the annular depression 15 and the distal end of the catheter 1, including shoulder 17. Thus, following deflation of the balloon 8, the catheter 1 may be withdrawn through the central lumen 19 of stent 18 leaving the expanded stent 18 in place within the prostatic urethra, as will be detailed infra in connection with the method of the present invention.

The outer diameter of the catheter is preferably minimized, to facilitate insertion and to avoid side effects and complications resulting from stretching of the urethra. There may be provided in accordance with the present invention a graduated set of graft-catheter systems with different sizes to suit individual patient requirements.

The catheter may be provided with a flexible, resilient catheter tip 20 at the distal end thereof. The tip 20 is preferably formed with a tapered or rounded configuration to minimize damage to the urethral lining and further to ease in insertion of the catheter into the collapsed lumen of the urethra.

Expansion Catheter of FIGS. 9-11

Another embodiment of an expansion catheter according to the present invention is illustrated in FIGS. 9-11. In this embodiment, there is provided an elongate catheter shaft 2 having an elastic sheath 21 disposed therearound. The shaft comprises an elongate sleeve 22 having a female thread 23 on the interior thereof. Rotatably positioned within the sleeve 22 is an elongate shaft 24 having a male thread 25 for engaging the female thread 23 on sleeve 22. The threaded region, illustrated in FIG. 11 near the distal ends of shaft 24 and sleeve 22, extends in an axial direction for a sufficient distance to permit the expansion member 32 to be fully drawn into the conical space 34 as will become apparent. In the illustrated embodiment, a first knob 26 is rigidly secured to the proximal end of shaft 24, and a second knob 27 is secured to the proximal end of sleeve 22.

A plurality of axially oriented floating segments or tines 28 are movably disposed distal to the end of sleeve 22. The exterior surfaces 29 of the tines 28 are held in place by the elastic sheath 21 and cooperate to form a generally cylindrical exterior profile, for receiving an unexpanded tubular stent 18. The radial thickness of the tines 28 tapers from the thickest dimension near the proximal end 30 of tine 28 to the thinnest dimension near the distal end 31 of tine 28, thereby defining a roughly cone-shaped interior space 34.

A cone-shaped expansion member 32 is attached by its pointed end to elongate shaft 24. Rotation of knob 26 in a first direction relative to knob 27 draws elongate shaft 24 axially in a proximal direction, moving expansion member 32 into the cone-shaped space 34 formed by the tines 28. Further rotation of knob 26 in a first direction relative to knob 27 results in expansion member 32 effecting a radial outward expansion of tines 28, which in turn causes a radial outward expansion of the expandable stent 18. Rotating the knob 26 in the reverse relative direction causes expansion member 32 to back out of the space 34. The resilient nature of the elastic sheath 21 causes tines 28 to return back to their unexpanded configuration, when permitted by movement of member 32 in a distal direction. The tubular elastic sheath 21 extends beyond the end of expansion member 32 at which point it merges with an integrally formed blunt end 33. As illustrated in FIG. 11, the outer diameter of blunt end 33 and of the sheath 21 proximal to stent 18 are slightly enlarged so that the exterior configuration of the expansion catheter, with the stent mounted thereon is substantially uniform and generally smooth along its axial length.

Stent Removal Apparatus

Another aspect of the present invention provides an apparatus for removing a previously positioned and expanded stent, under direct endoscopic vision. Referring to FIGS. 12-14, the apparatus comprises a catheter shaft 35, having proximal and distal attachment means 36, 37 attached thereto and adapted to engage the corresponding proximal and distal ends 38, 39 of the implanted stent. The attachment means are capable of movement, relative to each other, along the axial direction of the removal instrument.

In the illustrated embodiment, the proximal attachment means 36 comprises a plurality of tines 40, inclined in the proximal direction and mounted to a sleeve 41 which extends the length of the catheter shaft 35. A first knob 42 is secured to the proximal end of sleeve 41, in proximity with a second knob 43 attached to the proximal end of an elongate shaft 44 which extends through sleeve 41. The interior surface of sleeve 41 may be provided with a female thread for engaging a male thread on the shaft 44, in the manner illustrated in FIG. 11, illustrating an expansion catheter of the present invention. The important relationship is that the shaft 44 is capable of reciprocating movement within the sleeve 41, as will become apparent.

The distal attachment means 37 comprises a ring 45 which is rotatably attached near the distal end of shaft 44 by engaging an annular groove on said shaft 44 or other conventional means. A plurality of tines 46 are attached to the ring 45, said tines 46 radiating outward and inclined in a distal direction.

An outer sheath 47 is slidably mounted on the outside of sleeve 41. The interior lumen of sheath 47 is flared at the distal end 48 thereof so that the sheath 47 may be slid down over tines 40, causing them to resiliently bend radially inwardly yet remain inclined in the proximal direction. To help ensure that the tines 40 are not bent towards the distal direction by the sheath 47, the outer surface of tines 40 may be provided with a rounded edge 49. The mechanical features of the removal instrument will be made more clear by reference to the discussion of the method of removing an implanted stent, infra.

Expandable Tubular Stent

Referring to FIG. 4, there is illustrated a radially expandable tubular stent 18 according to the present invention, the stent being illustrated in its unexpanded, substantially cylindrical configuration and mounted on a balloon catheter. The wall thickness of the stent is advantageously from about 0.003 to about 0.06 inches, preferably is from about 0.005 to about 0.025 inches, and more preferably is from about 0.008 to about 0.012 inches. The wall of the stent is formed with a plurality of passages therethrough, as best illustrated in FIGS. 6, 7 and 8, which depict wall patterns as they might appear if the wall of the stent 18 were rolled out flat. In FIG. 6, a first plurality of parallel filaments 50 are aligned at a diagonal to a second plurality of parallel filaments 51, all formed from a single piece of material to yield a diamond pattern having a plurality of diamond shaped openings 52 therethrough. This configuration of the filaments 50 and 51 permits radial outward deformation of the tubular stent 18 in response to a radial outward force exerted by the expansion catheter 1 of the present invention. Construction of the stent from a malleable, biologically compatible metal such as titanium, or other materials discussed infra permits the stent 18 to hold its expanded configuration under stress exerted by, for example, a hypertrophied prostate gland, thereby maintaining patency in an otherwise stenotic or occluded lumen. In addition, orientation of filaments 50 and 51 is such that forces exerted upon the axial ends 38, 39 of an expanded tubular stent 18 in opposite axial directions will effect an axial elongation of the stent 18 and a consequent reduction in the diameter thereof.

A variation of the wall pattern of FIG. 6 is illustrated in FIG. 8, wherein the roughly diamond shaped openings become smaller near the axial ends of the stent 18. This configuration facilitates greater expansion in the central region 64 thereof, and, like the pattern in FIG. 6, permits the expanded stent 18 to be reduced in diameter by applying an axially elongating force thereto.

The ratio of solid wall area to the total area of the opening therethrough is relatively low. This minimizes contact area between the material of the stent and the lining of the lumen, may improve the expansion characteristics of the stent, and minimizes interference with vessels entering the urethral lumen from the side, such as the prostatic ducts, and the terminal portion of the ductus deferens, which traverses the prostate to empty into the urethra. In addition, the transverse openings through the wall of the stent may promote tissue ingrowth thereby minimizing encrustation of the filament portions 50 and 51, of the stent by dissolved minerals, and reducing the risk of migration of the stent in the direction of the bladder.

Optimally, the wall thickness of any given stent will be substantially uniform throughout, however, in one embodiment of the present invention, the wall is thinner in the central region 64. The thickness of the stent wall as measured in the radial direction may be different in different stents in order to permit a greater or lesser area of transverse openings therethrough, while maintaining structural integrity of the stent. It is important that the stent 18 be capable of withstanding the constant radially inward directed force exerted by a hypertrophied prostate gland.

The axial length of the stent 18 should be sufficient that pressure exerted by the hypertrophied prostate cannot cause stenosis of the lumen beyond the axial ends thereof. The length of the stent will often be from about 1 cm to about 4 cm, depending upon the location and extent of the hypertrophy or hyperplasia, is preferably from about 1.5 to about 3.0 cm in length and most preferably is about 2.4 cm in length, which is the average approximate length of the prostatic urethra.

Preferably the stent of the present invention will be made using a biocompatible material, either throughout, or in the form of a coating over the stent, which will improve its compatibility with the physiological and chemical environment within the urethral lumen. For example, the stent will be exposed to urine having a pH in the range of from about 4.5 to 8, a relatively wide variation compared to other body fluids such as blood, which generally has a pH of about 7.4. The coating may be a plastic or polymeric material, such as a fluoropolymer, for example polytetrafluoroethylene, or preferably silicone rubber. Alternatively, the coating may be isotropic carbon, and the surface of the stent may be either smooth or microporous in nature. It is believed that a smooth surface is desirable because irregularities in the surface may provide sites for precipitation of salts due to the relatively high osmolality of urine. A sufficiently smooth surface would thus minimize encrustation of the stent. A surfactant or chelating agent may advantageously be affixed to the surface of the stent, for further reducing encrustation thereof.

The maximum expanded diameter of the stent 18 will likely be within the range of from about 10 mm to about 14 mm or greater. This range refers to the largest crosssectional dimension in the case of stents which are enlarged to a configuration having a non-circular cross section or a non-cylindrical profile. Depending upon its construction material and physical design, a given stent may be expanded within an optimal range, which may be less than the overall ranges indicated above.

Figure 18:
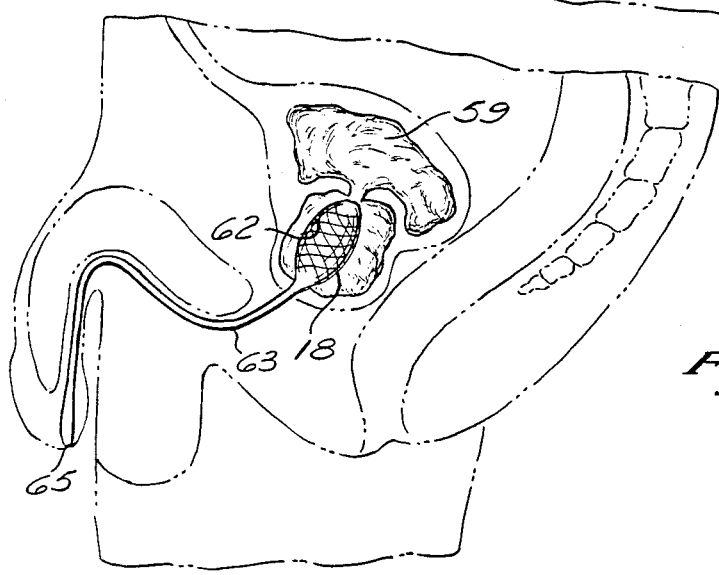
FIG. 18 is the sectional view of FIG. 16, illustrating another embodiment of the expanded stent of the present invention within the prostatic urethra.

The stent 18 of the present invention may be expanded from a first, unexpanded configuration to a second, expanded state having a substantially uniform cross section throughout the axial length thereof, or to a configuration having a greater cross-sectional area in the central region than in the regions near the axial ends thereof. This latter configuration is achieved, for example, by a mechanical design of the stent 18 which permits greater expansion in the central region, such as by slotting with greater frequency in the case of a malleable metal stent, or by choice of a material for the central region of the stent having greater expansion abilities than a different material incorporated into the axial end regions 38 and 39. For example, the sidewall pattern illustrated in FIG. 8 would permit greater radial expansion near the center than at the axial ends. Alternatively, graduated wall thicknesses on a stent of uniform composition could be employed. Preferably, however, the configuration of the expanded stent 18 corresponds to the expanded shape of the balloon 8 used to accomplish its expansion. Thus, the catheter 1 of the present invention may be provided with balloons 8 having a variety of fully inflated profiles, for example, cylindrical, concave, convex, or frusto-conical, to suit any of a variety of clinical indications. FIGS. 15 and 18, for example, illustrates a stent that has been expanded by a balloon having a convex profile.

In the embodiment illustrated in FIGS. 15 and 18, migration of the stent 18 is minimized due to the restrictive forces caused by the normal tissue in the area of the bladder neck. The enlarged midsection 64 of the stent 18 would be unable to pass through the restricted neck of the bladder because any forces tending to cause migration would generally be insufficient to force a stent of this configuration axially through the urethra. For similar reasons, migration of the stent away from the bladder would also be minimized.

In addition, the stent is advantageously expanded to have an oval or otherwise non-circular cross-sectional area, such as that illustrated in FIG. 7. The stent is advantageously expanded to have a configuration which closely approximates the cross-sectional shape of the native prostatic urethra, and may permit normal contractions of the prostate gland.

According to another embodiment of the stent 18 of the present invention, the axial end regions 38, 39 of the stent 18 are softer or more flexible than the region in the center of the stent 18 thereby allowing a smooth transition from the lumen 19 of the stent 18 to the lumen of the urethra. The axial end regions 38, 39 of the stent may be formed with a gradual taper in a radial inward direction, thereby reducing the risk of stress and irritation, and possibly even kinking of the urethral lining at the graft-urethra lumen juncture.

Referring to FIG. 16, there is illustrated in simplified form a sectional view of the male pelvic region, showing the bladder 59, an enlarged or hypertrophied prostate gland 60 causing a stenosis 61 of the prostatic urethra 62. Thus, the interior diameter of the prostatic urethra 62 has become smaller than the interior diameter of the non-prostatic urethra 63.

Figure 17:
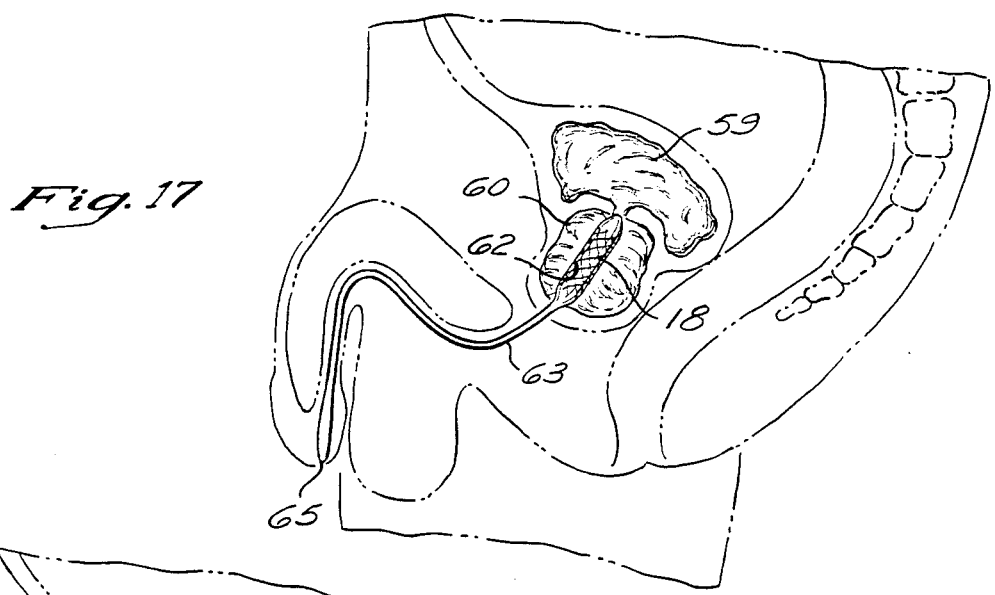
FIG. 17 is the sectional view of FIG. 16, illustrating an expanded stent of the present invention within the prostatic urethra.

Referring next to FIG. 17, there is illustrated an expanded stent 18 within the prostatic urethra 62, having a substantially uniform cross section throughout the midsection 64 thereof, and a radially inwardly directed taper near the axial ends 38 and 39. The expanded state diameter of the stent 18 is slightly exaggerated for illustration. Referring to FIG. 18, there is illustrated an expanded stent 18 in position within the prostatic urethra 62, having a generally convex exterior configuration throughout its axial length. In this latter preferred inflated state configuration, the resilient force exerted by the prostate gland 60 acts in cooperation with the generally convex stent 18 to minimize the likelihood of migration of stent 18 into the interior of bladder 59, or into the urethra 63 downstream of the prostatic urethra 62.

A malleable metal stent according to the present invention, comprising, for example, titanium, may be manufactured by first machining titanium tube or sheet stock to the desired wall thickness, generally in the range of from about 0.004 to about 0.05 inches, and then cutting or etching the wall pattern thereon, such as one of those patterns illustrated in FIGS. 6, or 8. The cutting may advantageously be accomplished using a laser system, such as a Koppers Laser System marketed by the Laser Systems Division of Koppers Company, Inc., of Westminster, Md. Tube stock may be laser cut on a revolving mandrel, whereas sheetstock may be laser cut in sheet form and subsequently rolled into tubular form, welded, and polished.

Method of Placement and Dilation of Expandable Tubular Stent

In accordance with the insertion method of the present invention, a dilation means 1 having a suitable expandable stent 18 associated therewith is selected and then transurethrally positioned within the prostatic urethra 62 by way of the external opening 65 of the urethra 63. The positioning step may advantageously be accompanied by or preceded by the introduction of a radiopaque dye through dye port 14, from which it will be conducted via lumen 12 through the catheter 1 to the area of stenosis 61, to enable visualization thereof. The positioning step may also advantageously be preceded by coating the catheter 1 and stent 18 disposed thereon with a water soluble surgical jelly or other lubricant, such as Surgilube ®, a sterile, bacterio-static surgical lubricant, available from E. Fougera & Co., Melville, N.Y. Positioning may also be accomplished with the use of a guidewire 13, in accordance with known catheterization techniques.

With the balloon catheter 1 in position, a pressurized fluid is introduced into inflation port 3 which, by way of lumen 5 and inflation duct 9 enters the balloon 8. Vent port 4 may be vented until all air has been purged, at which time it is sealed by closing a stopcock or other conventional means. Inflation of the balloon 8 causes radial expansion of the expandable stent 18 and also dilation of the surrounding lumen against the pressure exerted by the hypertrophied prostate gland 60. The radially expandable stent 18 is advantageously dilated sufficiently that the inside diameter of the lumen 19 therethrough exceeds the outer diameter of the region of the catheter between the annular depression 15 adapted to receive the undilated stent 18 and the distal tip 20 of the catheter 1, so that the catheter 1 may be withdrawn through the lumen 19 of the expanded stent 18 leaving said stent 18 in place within the prostatic urethra.

By varying the configuration of the balloon 8 in the case of a balloon catheter, as previously discussed, the stent 18 may be expanded to a final shape having a substantially circular cross section, or a cross section that more closely adheres to the natural configuration of the normal lumen inside the urethra.

Following dilation of the intraluminal stent 18, the dilating catheter 1 may be reduced in diameter by exhausting the pressurizing fluid under any contractile force of the balloon 8 and then evacuating the contents of the balloon 8 by way of inflation port 3. The apparatus may then be withdrawn through the lumen 19 of stent 18, leaving the expanded stent 18 in place within the prostatic urethra 62, illustrated in FIGS. 17 and 18.

Method for Subsequent Dilation of Expandable Tubular Stent

The apparatus 1 may at a later time be reinserted, via the external opening 65 of the urethra 63, should it become necessary to further increase the diameter of the stent 18 within urethral lumen 62 or to redilate the expandable stent 18. According to this aspect of the process of the present invention, a previously positioned and dilated stent 18 is fluoroscopically visualized in accordance with known techniques. An appropriate catheter 1 having a balloon 8 with the desired inflated state configuration is selected, transurethrally inserted as discussed supra, and positioned with the deflated balloon 8 coaxially disposed within the prepositioned, expanded stent 18. For this purpose, the catheter 1 may be provided with one or more radiopaque markers 66 for visualization of the location of the balloon 8. The balloon 8 is then inflated, re-expanding, further expanding, or altering the configuration of the stent 18. Thereafter, the balloon 8 may be deflated, and the catheter 1 is withdrawn, leaving the re-expanded stent 18 within the prostatic urethra 62.

Method for Removal of Expanded Tubular Stent

In yet a further aspect of the process of the present invention, a prepositioned stent 18 may be removed through the use of a removal instrument equipped such as that illustrated in FIG. 12 with attachment means 36 and 37, described supra, and adapted for insertion through the operating channel of a urethroscope or cystoscope. The urethroscope is transurethrally inserted, by way of the external opening 65 of the urethra 63, and positioned such that the previously positioned stent 18 may be directly visually observed. Under direct observation, the removal instrument is positioned coaxially within the prepositioned stent 18 by way of the operating channel of the urethroscope. During this positioning step, the sheath 47 is slid axially in a distal direction to cover distal attachment means 37. When both attachment means 36 and 37 are positioned within the lumen 19 of an expanded stent 18, the sheath 47 is axially retracted, exposing said attachment means 36 and 37. The tines 40 and 46 resiliently bend in a radial outward direction in the absence of sheath 47, until they reach approximately a diagonal as illustrated in FIG. 13. As shaft 44 is axially extended, e.g. by rotating knob 43 while knob 42 is held stationary, the proximal tines 40 will engage the proximal end 38 of the stent 18 by extending through the openings 52 or 58 illustrated in FIGS. 6 and 7. In a similar manner, the distal attachment means 37 is caused to engage the distal end 39 of the stent 18. The attachment means are thereafter moved further apart in an axial direction, causing an axial elongation of the implanted stent 18. Due to the configuration of the side wall of the stent 18, a reduction in the radius of the stent 18 results. Once sufficiently reduced in diameter, the sheath 47 is slid distally to cover both attachment means 36 and 37, having the radially reduced stent 18 attached therebetween. The urethroscope and the removal instrument, having the elongated stent 18 still engaged, may thereafter be transurethrally withdrawn.

Although this invention has been described in terms of certain preferred embodiments, other embodiments that are apparent to those of ordinary skill in the art are also within the scope of the invention. Accordingly, the scope of the invention is intended to be defined only by reference to the appended claims.

What is claimed is:

1. A method for treating hypertrophy of the prostate gland, comprising the steps of:
    positioning a dilation means having an expandable tubular stent associated therewith within the prostatic urethra; said dilation means comprising a catheter having a circumferential recess thereon in which an expandable balloon is mounted, wherein said stent is positioned over said balloon in said recess, and wherein said positioning step includes protecting the urethral lining from damage by minimizing sliding contact with said stent by maintaining said stent in said recess during said positioning;
    dilating the expandable tubular stent with said dilation means to deform said stent, to expand the prostatic urethra, and to maintain such expansion against radial inward forces generated by said prostate;
    restoring said dilation means to its substantially unexpanded state; and
    removing said dilation means and leaving the dilated tubular stent within the urethra.

2. A method as in claim 1, wherein said positioning step comprises the transluminal insertion of said dilation means, by way of the external opening of the urethra, without the use of a sheath.

3. A method as in claim 1, further comprising the step of introducing a radiopaque dye for fluoroscopic visualization.

4. A method as in claim 1, further comprising the initial step of selecting a balloon catheter having an expanded configuration of the balloon corresponding to the interior configuration of the native prostatic urethra, prior to stenosis by prostatic hypertrophy.

5. A method as in claim 1, wherein said stent comprises a biologically inert material.

6. A method as in claim 1, wherein the radial dilation of said stent results in a substantially uniform cross-sectional area along its axial length.

7. A method as in claim 1, wherein said stent is outwardly radially expanded to a greater final cross-sectional area in a central region than at the axial ends thereof.

8. A method as in claim 7, wherein said stent in its expanded state comprises a non-circular cross section.

9. A method as in claim 2, further comprising an initial step of inserting a guidewire prior to the transluminal insertion of said dilation means.

10. The method of claim 1, wherein the diameter of said catheter on either side of said recess is at least about as great as the unexpanded diameter of said stent.

11. The method of claim 10, wherein said catheter and said unexpanded stent mounted thereon together form a substantially cylindrical configuration.

12. A method as in claim 1, further comprising the steps prior to said positioning step of:
providing a plurality of balloon catheters having different expanded configurations, and
selecting said dilation means from among said balloon catheters.

13. The method of claim 12, further comprising the steps after said removing step of repeating the providing, selecting, positioning, dilating, restoring and removing steps of claim 39, wherein the balloon catheter selected in said repeated steps has a different expanded configuration than the balloon catheter first selected.

14. An apparatus for relieving the symptoms of prostatic hypertrophy, comprising:
an axially elongate catheter shaft having a proximal and a distal end of a size suitable to be inserted in a human urethra;
an inflation port at the proximal end of said catheter shaft, in fluid communication with a radially expandable balloon disposed near the distal end of said catheter shaft by means of a first lumen extending axially therethrough;
a vent port at the proximal end of said catheter shaft in fluid communication with said expandable balloon by means of a second lumen extending axially through said catheter shaft;
a removably mounted, radially outwardly expandable tubular supportive stent coaxially disposed about the expandable balloon, said stent being formed from a malleable material which is biologically compatible with a urethra and comprising an opening at each end and a central lumen therethrough;
wherein said stent is radially deformable from a first unexpanded state to a second, expanded deformed state in response to pressure from said balloon and is capable of withstanding said expanded, deformed configuration against inward forces exerted from a hypertrophied prostate; and
the outer diameter of the stent in its first, unexpanded state is not substantially greater than the outer diameter of the adjacent catheter shaft, the catheter shaft and stent mounted thereon thereby having a substantially uniform cylindrical profile such that the apparatus may be transurethrally positioned within the prostatic urethra by way of the external opening of the urethra with said stent substantially totally exposed to the wall of the urethra, without the use of a sheath, and with said stent substantially totally exposed to the wall of the urethra.

15. An apparatus for relieving the symptoms of hypertrophy of the prostate gland, comprising:
an axially elongate catheter shaft;
an expandable region on said shaft disposed near the distal end of said shaft;
a removably mounted, radially outwardly expandable tubular stent disposed on top of said expandable region and adapted for insertion into the prostatic urethra; and
means on said catheter shaft for protecting the urethral lining from damage due to sliding contact with said stent, said protecting means comprising at least one circumferential shoulder on said catheter abutting said stent and said expandable region, the diameter of said shoulder being at least as great as the diameter of said stent so that said stent does not extend radially beyond said shoulder, wherein said stent is radially expandable by deformation thereof to a preselected stable configuration in response to pressure from said expandable region on said shaft.

16. An apparatus for relieving the symptoms of hypertrophy of the prostate gland, comprising:
an axially elongate catheter shaft comprising at least one lumen therethrough and having an annular recess thereon for receiving a stent;
an expandable balloon mounted on said shaft in said recess and in communication with said lumen; and
a removably mounted, radially outwardly deformable and expandable tubular stent coaxially disposed about said balloon and situated in said recess, wherein said stent has an opening at each axial end and a central lumen therethrough,
wherein said stent is radially expandable by deformation to a preselected configuration in response to pressure from said balloon, and the outside diameter of the stent, in its unexpanded state, is not substantially greater than the outside diameter of the adjacent catheter shaft.

17. An apparatus for relieving symptoms of hypertrophy of the prostate gland, comprising:
an axially elongate catheter shaft having at least one lumen therethrough and having a circumferential recess near one end thereof;
an expandable balloon mounted on said shaft in said recess and in communication with said lumen;
a removably-mounted, radially outwardly expandable tubular stent coaxially disposed about said balloon, said stent having an opening at each end and a central lumen therethrough;
wherein said stent is radially expandable by deformation thereof to a preselected configuration in response to pressure from said balloon, and wherein the outside diameter of the stent, in its unexpanded state, is not substantially greater than the outside diameter of the adjacent catheter.

18. An apparatus as in claim 17, wherein said balloon in its expanded state, has a non-cylindrical configuration.

19. An apparatus as in claim 17, wherein said balloon in its expanded state has a non-circular cross section along its axial length.

20. An apparatus as in claim 17, wherein said balloon in its expanded state has a smaller cross-sectional area at its axial ends than in the central region thereof.

21. An apparatus as in claim 17, wherein the expanded cross-sectional area of said stent is unresponsive to the radial inward pressure responsible for the stenosis of the urethra.

22. An apparatus as in claim 17, wherein said catheter further comprises a lumen for receiving a steerable guidewire therethrough.

23. An apparatus as in claim 17, further comprising at least one radiopaque marker associated with the axial position of said balloon.

24. An apparatus as in claim 17, wherein said balloon expands to a configuration having a non-circular cross section, and a convex profile along its axial length.

25. An apparatus as in claim 17, further comprising a biocompatible, essentially smooth coating on said stent.

26. An apparatus as in claim 25, wherein said coating comprises silicone rubber.

27. An apparatus as in claim 17, wherein said stent further comprises a flexible, resilient region at each axial end thereof.

28. An apparatus as in claim 17, further comprising a lubricant coating around said tubular stent.

* * * * *